US00PP29260P2

(12) United States Plant Patent
Nguyen

(10) Patent No.: US PP29,260 P2
(45) Date of Patent: Apr. 24, 2018

(54) ***ANGELONIA* PLANT NAMED 'BALANGSPIRD'**

(50) Latin Name: *Angelonia angustifolia*
Varietal Denomination: Balangspird

(71) Applicant: Ball Horticultural Company, West Chicago, IL (US)

(72) Inventor: Phuong N. Nguyen, Thousand Oaks, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/530,880

(22) Filed: Mar. 13, 2017

(51) Int. Cl.
*A01H 5/02* (2018.01)

(52) U.S. Cl.
USPC ..... Plt./404
CPC ..... *A01H 5/02* (2013.01)

(58) Field of Classification Search
USPC ..... Plt./404
CPC ..... A01H 5/02
See application file for complete search history.

*Primary Examiner* — Kent L Bell
(74) *Attorney, Agent, or Firm* — Audrey Charles

(57) ABSTRACT

A new and distinct cultivar of *Angelonia* plant named 'Balangspird', characterized by its medium violet and white bicolored flowers, dark green-colored foliage, and moderately vigorous, prostrate-spreading growth habit, is disclosed.

1 Drawing Sheet

Latin name of genus and species of plant claimed: *Angelonia angustifolia.*

Variety denomination: 'Balangspird'.

BACKGROUND OF THE INVENTION

The present invention relates to a new and distinct cultivar of *Angelonia* plant botanically known as *Angelonia angustifolia* and hereinafter referred to by the cultivar name 'Balangspird'.

The new cultivar originated in a controlled breeding program in Arroyo Grande, Calif. during September 2012. The objective of the breeding program was the development of *Angelonia* cultivars having continuous flowering and a prostrate-spreading growth habit.

The new *Angelonia* cultivar is the result of cross-pollination. The female (seed) parent of the new cultivar is the proprietary *Angelonia angustifolia* breeding selection coded PN5694-2, not patented, characterized by its light pink and white bicolored flowers, dark green-colored foliage, and moderately vigorous, spreading growth habit. The male (pollen) parent of the new cultivar is the proprietary *Angelonia angustifolia* breeding selection coded PN5743-5, not patented, characterized by its medium purple and orchid bicolored flowers, dark green-colored foliage, and moderately vigorous, spreading growth habit. The new cultivar was discovered and selected as a single flowering plant within the progeny of the above stated cross-pollination during March 2013 in a controlled environment in Arroyo Grande, Calif.

Asexual reproduction of the new cultivar by terminal stem cuttings since March 2013 in Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balangspird' as a new and distinct cultivar of *Angelonia* plant:

1. Medium violet and white bicolored flowers;
2. Dark green-colored foliage; and
3. Moderately vigorous, prostrate-spreading growth habit.

Plants of the new cultivar differ from plants of the female parent primarily in flower color and in having larger-sized flowers and from plants of the male parent primarily in flower color.

Of the many commercially available *Angelonia* cultivars, the most similar in comparison to the new cultivar is ANGELMIST Spreading Dark Purple 'Balangsparkl', U.S. Plant Pat. No. 25,558. However, in side by side comparisons, plants of the new cultivar differ from plants of 'Balangsparkl' in at least the following characteristics:

1. Plants of the new cultivar have darker colored foliage than plants of 'Balangsparkl'; and
2. Plants of the new cultivar have a bicolor flower petal color unlike plants of 'Balangsparkl'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balangspird'. The plants were grown in 4.5-inch pots for 9 weeks in a greenhouse in West Chicago, Ill. Plants were given one pinch at transplant.

DETAILED BOTANICAL DESCRIPTION

Figure 1:
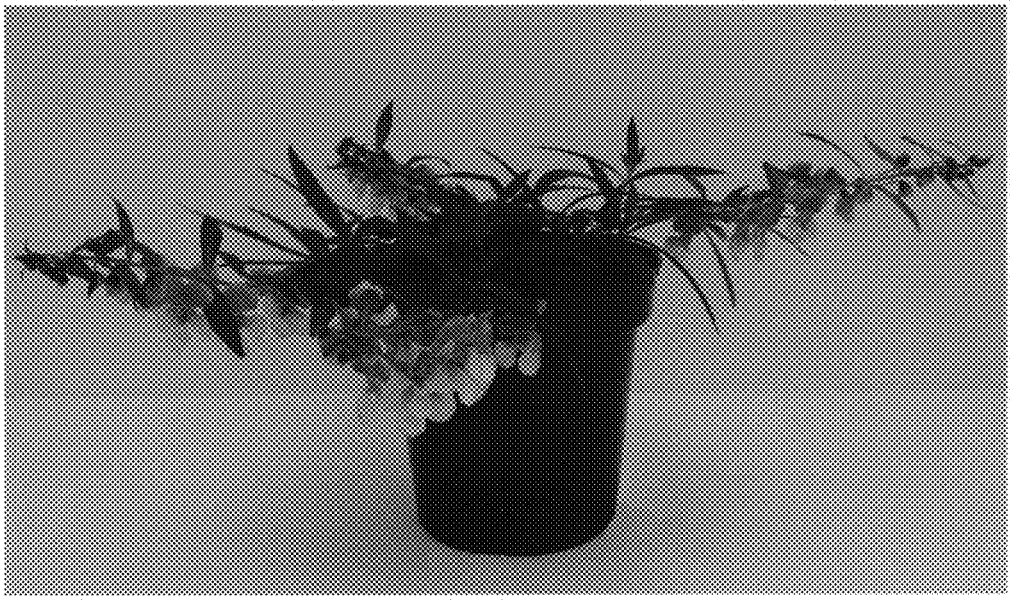
FIG. 1 illustrates a side view of the overall growth and flowering habit of 'Balangspird'.
Figure 2:
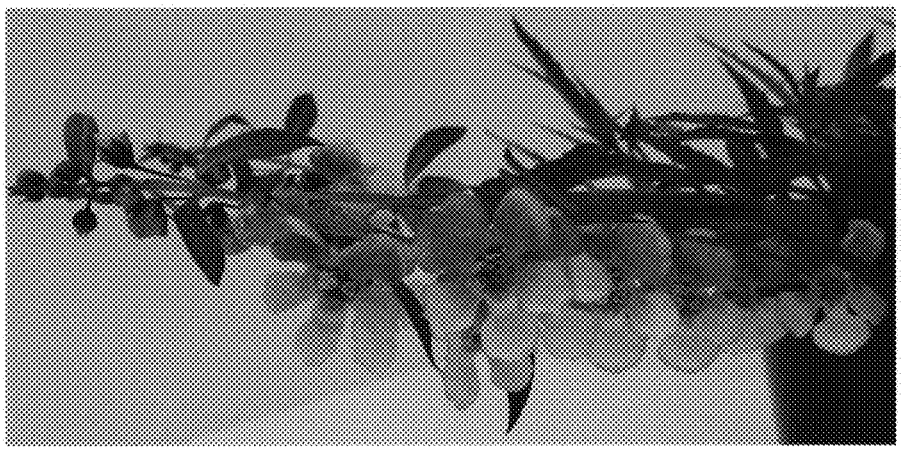
FIG. 2 illustrates a close-up view of an individual inflorescence of 'Balangspird'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in December 2016 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4.5-inch pots for 9 weeks utilizing a soilless growth medium. Plants were given one pinch at transplant. Greenhouse temperatures were maintained at approximately 66° F. to 70° F. (19° C. to 21° C.) during the day and approximately 58° F. to 62° F. (14° C. to 17° C.) during the night. Greenhouse light levels of 2,500 footcandles to 6,000 footcandles were maintained during the day. Measurements and numerical values represent averages of typical plants.

Botanical classification: *Angelonia angustifolia* cultivar Balangspird.

Parentage:

*Female parent*.—Proprietary *Angelonia angustifolia* breeding selection coded PN5694-2, not patented.

*Male parent*.—Proprietary *Angelonia angustifolia* breeding selection coded PN5743-5, not patented.

Propagation:

*Type cutting*.—Terminal stem.

*Time to initiate roots*.—Approximately 7 to 9 days.

*Time to produce a rooted cutting*.—Approximately 21 to 28 days.

*Root description*.—Fine, fibrous.

*Rooting habit*.—Freely branching.

Plant description:

*Commercial crop time*.—Approximately 4 to 6 weeks from a rooted cutting to finish in a 10 cm pot.

*Growth habit and general appearance*.—Moderately vigorous, prostrate- spreading.

*Size*.—Height from soil level to top of plant plane: Approximately 6.0 cm. Width: Approximately 30.5 cm.

*Branching habit*.—Freely branching, pinching improves basal branching. Quantity of main branches per plant: Approximately 4.

*Branch*.—Shape: Square in cross section. Strength: Moderately strong, somewhat flexible. Length: Approximately 18.0 cm. Diameter: Approximately 2.5 mm. Length of central internode: Approximately 1.4 cm. Texture: Glabrous. Color of young and mature stems: 146B.

Foliage description:

*General description*.—Quantity of leaves per main branch: Approximately 22. Fragrance: None. Form: Simple. Arrangement: Opposite.

*Leaves*.—Aspect: Primarily perpendicular or obtuse angle to stem. Shape: Narrowly elliptic. Margin: Widely serrate. Apex: Acute. Base: Sessile, Venation pattern: Pinnate. Length of mature leaf: Approximately 6.3 cm. Width of mature leaf: Approximately 1.1 cm. Texture of upper and lower surfaces: Glabrous. Color of upper surface of young foliage: 137A with indistinguishable venation. Color of lower surface of young foliage: 137B with midvein of 146D, other venation indistinguishable. Color of upper surface of mature foliage: Closest to 139A with indistinguishable venation. Color of lower surface of mature foliage: Closest to 137B with midvein of 146D, other venation indistinguishable.

Flowering description:

*Flowering habit*.—'Balangspird' is freely flowering under outdoor growing conditions with substantially continuous blooming from spring through autumn and year-round in greenhouse environment.

*Lastingness of individual flower on the plant*.—Approximately 7 to 10 days.

Inflorescence description:

*General description*.—Type: Terminal raceme. Quantity per plant: Approximately 4. Fragrance: Slight, sweet. Length: Approximately 13.0 cm. Width: Approximately 4.0 cm. Quantity of fully open flowers per inflorescence: Approximately 12.

Flower description:

*Type*.—Solitary, zygomorphic.

*Bud*.—Rate of opening: Generally takes 3 to 4 days for bud to progress from first color to fully open flower.

*Bud just before opening*.—Shape: Globular. Length: Approximately 6.0 mm. Diameter: Approximately 6.0 mm. Color of upper surface: 145A. Color of lower surface: 146B.

*Corolla*.—Shape: Bilabiate. Aspect: Facing outward. Length: Approximately 2.5 cm. Width: Approximately 2.0 cm. Depth: Approximately 9.0 mm.

*Petals*.—Quantity: 5 petals fused at base forming a throat and consisting of an upper lip with 2 petals and a lower lip with 3 petals, consisting of 2 lateral petals and one central petal. Shape: Obovate. Margin: Entire. Apex: Obtuse.

*Upper lip*.—Length of petals from throat: Approximately 8.0 mm. Width of each petal: Approximately 1.1 cm. Texture of upper surface: Moderately glandular pubescent. Texture of lower surface: Sparsely glandular pubescent. Gland color: Colorless, transparent. Color of upper surface when fully open: 86B. Color of lower surface when fully open: 86D.

*Lower lip, lateral petals*.—Length of petals from throat: Approximately 9.0 mm. Width of each petal: Approximately 9.0 mm. Texture of upper surface: Moderately glandular pubescent. Texture of lower surface: Densely glandular pubescent. Gland color: Colorless, transparent. Color of upper surface when fully open: NN155D with 86B at base and margin. Color of lower surface when fully open: NN155D with 86D at base and margin.

*Lower lip, central petal*.—Length from the palate: Approximately 9.0 mm. Width: Approximately 1.0 cm. Texture of upper surface: Moderately glandular pubescent. Texture of lower surface: Densely glandular pubescent. Gland color: Colorless, transparent. Color of upper surface when fully open: NN155D with 86B at margin. Color of lower surface when fully open: NN155D with 86D at margin.

*Throat*.—Length: Approximately 7.0 mm. Width: Approximately: 4.0 mm. Texture of inner and outer surfaces: Glabrous. Color of inner surface: NN155D with spots of N79A and two circular areas of 146A above palate. Color of outer surface: NN155D with spots of N79A and a faint central spot of 146D. Palate color: NN155A and 145A. Palate texture: Glabrous. Teeth color: 155A.

*Calyx*.—Shape: Star, cupped. Diameter: Approximately 6.0 mm.

*Sepals*.—Quantity per flower: 5, fused at base. Shape: Ovate, Apex: Acute. Length: Approximately 4.0 mm. Width: Approximately 1.5 mm. Texture of upper (inner) and lower (outer) surfaces: Sparsely glandular pubescent. Gland color: Colorless, transparent. Color of upper (inner) surface: 137A. Color of lower (outer) surface: 137A with a heavy overlay of 187A.

*Pedicel*.—Strength: Strong, flexible. Aspect: Acute angle to stem. Length: Approximately 1.6 cm. Diameter: Approximately 0.5 mm. Texture: Glabrous. Color: 146A with a heavy overlay of 187A.

*Reproductive organs*.—Androecium: Stamen quantity: 4 per flower. Filament length: Approximately 3.0 mm. Filament texture: Sparsely glandular pubescent. Gland color: Colorless, transparent. Filament color: NN155D with a faint overlay of 86D. Anther shape: Bilobed. Anther length: Approximately 1.0 mm. Anther color: 103D. Pollen amount: Abundant. Pollen color: 155D. Gynoecium: Pistil quantity: 1 per flower. Pistil length: Approximately 5.0 mm. Stigma shape: Pointed. Stigma length: Less than 1.0 mm. Stigma color: NN155D. Style length: Approximately 4.0 mm. Style color: NN155D. Ovary diameter: Approximately 1.0 mm. Ovary texture: Sparsely pubescent. Ovary color: 144A.

Seed and fruit production: Neither seed nor fruit production has been observed.

Disease and pest resistance: Resistance to pathogens and pests common to *Angelonia* has not been observed.

What is claimed is:

1. A new and distinct cultivar of *Angelonia* plant named 'Balangspird', substantially as herein illustrated and described.

* * * * *